United States Patent
Livingston et al.

(10) Patent No.: US 8,664,357 B2
(45) Date of Patent: Mar. 4, 2014

(54) SOLVENT RESISTANT DIAFILTRATION OF PEPTIDES, PNA OR OLIGONUCLEOTIDES

(75) Inventors: Andrew Guy Livingston, Knebworth (GB); Ludmila Georgieva Peeva, London (GB); Sheyung Wang Jerry So, London (GB); Renato Campos Vasconceles, London (GB); Robin John Leatherbarrow, Horne Horley (GB); Edward William Tate, London (GB); Piers Robert James Gaffney, London (GB)

(73) Assignee: Imperial Innovations Limited, London (GB)

( * ) Notice: Subject to any disclaimer, the term of this patent is extended or adjusted under 35 U.S.C. 154(b) by 28 days.

(21) Appl. No.: 13/058,002

(22) PCT Filed: Aug. 7, 2009

(86) PCT No.: PCT/GB2009/050990
§ 371 (c)(1),
(2), (4) Date: Feb. 7, 2011

(87) PCT Pub. No.: WO2010/015864
PCT Pub. Date: Feb. 11, 2010

(65) Prior Publication Data
US 2011/0245460 A1    Oct. 6, 2011

(30) Foreign Application Priority Data
Aug. 8, 2008 (GB) .................................. 0814519.5

(51) Int. Cl.
*B01D 61/14* (2006.01)
*C07H 1/06* (2006.01)
*C07K 1/06* (2006.01)
*C07K 1/34* (2006.01)

(52) U.S. Cl.
USPC ........ 530/335; 210/650; 530/344; 536/25.31; 536/25.4

(58) Field of Classification Search
None
See application file for complete search history.

(56) References Cited

U.S. PATENT DOCUMENTS 3,772,264 A    11/1973    Bayer et al.
4,006,078 A *  2/1977    Bickoff et al. ................ 426/425

(Continued)

FOREIGN PATENT DOCUMENTS

JP    57120599    7/1982
WO    03062452    7/2003

(Continued)

OTHER PUBLICATIONS

Christensen et al., "J Pept. Sci.", May-Jun. 1995; 1(3): pp. 175-183.

(Continued)

*Primary Examiner* — Jeffrey E Russel
(74) *Attorney, Agent, or Firm* — JWIP & Patent Services, LLC; Jacob G. Weintraub, Esq.

(57) ABSTRACT

According to the present invention, there is provided a process for the preparation of a first compound selected from peptides, oligonucleotides and peptide nucleic acids. The process comprises synthesizing the first compound and then separating the first compound formed in step (i) from a second compound, which is a reaction by-product of the synthesis of the first compound and/or an excess of a reagent used for the synthesis of a first compound by a process of diafiltration. The membrane used for the diafiltration process is stable in organic solvents and provides a rejection for the first compound which is greater than the rejection for the second compound.

12 Claims, 9 Drawing Sheets

(56) References Cited

U.S. PATENT DOCUMENTS

| | | | |
|---|---|---|---|
| 6,585,802 | B2 | 7/2003 | Koros et al. |
| 6,755,900 | B2 | 6/2004 | Koros et al. |
| 6,822,074 | B1 | 11/2004 | Jonczyk |
| 2007/0060688 | A1 | 3/2007 | Wang |
| 2007/0249806 | A1 | 10/2007 | Saksena |
| 2009/0012028 | A1* | 1/2009 | Chan et al. .................. 514/44 |

FOREIGN PATENT DOCUMENTS

| | | |
|---|---|---|
| WO | 2004055037 | 7/2004 |
| WO | 2005121164 | 12/2005 |
| WO | 2007125367 | 11/2007 |
| WO | 2007133700 | 11/2007 |

OTHER PUBLICATIONS

Bonora et al., "Bioconjugate Chem.", 1997, vol. 8 (6), pp. 793-797.
Wang X. et al., "J. Mem. Sci.", vol. 196, 2002, pp. 59-67.
Li, S. et al., "J. Mem. Sci.", vol. 222, 2003, pp. 191-201.
Tsuru T. et al., "Sep. Sci. and Technol.", vol. 29, 1994, pp. 971-984.
Vandezande Pieter et al, "Solvent Resistant Nanofiltration: Separating on a Molecular Level.", Chemical Society Reviews Feb. 2008, vol. 37, No. 2, Aug. 8, 2007.
Bayer E et al: "Liquid Phase Synthesis of Peptides", Nature, Nature Publishing Group, London, UK, vol. 237, No. 5357, Jun. 30, 1972.

* cited by examiner

SOLVENT RESISTANT DIAFILTRATION OF PEPTIDES, PNA OR OLIGONUCLEOTIDES

FIELD OF THE INVENTION

The present invention relates to a process for the preparation of compounds, in particular compounds selected from peptides, oligonucleotides and peptide nucleic acids.

BACKGROUND TO THE INVENTION

Peptides, oligonucleotides and peptide nucleic acids are biologically important molecules and comprise polymers made up of distinct repeat units. In the case of peptides the repeat units are amino acids or their derivatives, while in the case of oligonucleotides the repeat units are nucleotides or their derivatives. Oligonucleotides can be further divided into RNA oligonucleotides and DNA oligonucleotides, as is well known to those skilled in the art, see for example P. S. Millar, Bioconjugate Chemistry, 1990, Volume 1, pages 187-191. In the case of peptide nucleic acids (PNA) the backbone is composed of repeating N-(2-aminoethyl)-glycine units linked by peptide bonds. The various purine and pyrimidine bases are linked to the backbone by methylene carbonyl bonds. The sequence of the amino acids in a peptide, the sequences of RNA nucleotides in RNA or DNA nucleotides in DNA, or the sequence of purine and pyrimidine bases in PNA, determine the function and effects of the compounds in biological systems.

The compounds are synthesised through coupling together their repeat units to give a specific sequence. The repeat units may be protected at one or more reactive sites using protecting groups, to direct coupling reactions to a specific site on the protected repeat unit. Deprotection reactions may be required after a coupling reaction to remove protecting groups and prepare the compound for a subsequent coupling reaction. Synthesis takes place in a sequence of cycles, each cycle comprising a coupling reaction followed by a deprotection reaction. Between reactions the removal of traces of excess reagents and reaction by-products to very low levels is necessary to prevent erroneous sequences being formed in the sequence of repeating units. When the coupling or deprotection reactions are carried out in liquid phase, this purification is often tedious, and is achieved by time consuming precipitation, crystallisation, or chromatography operations. The chemistries and methods available for coupling and deprotection of peptides, oligonucleotides and peptide nucleic acids have been well documented.

Peptide synthesis was revolutionised in 1963 by the advent of solid phase synthesis (Merrifield R B J Am Chem Soc 8.5, (1963) 2149). In this approach, the first amino acid in a sequence is bound to a resin bead. Subsequent amino acids are coupled to the resin bound peptide, and finally, when the desired peptide has been grown, it is cleaved from the resin. Importantly, at the end of each coupling or deprotection reaction, residual unreacted protected amino acids, excess reagents, and other side products can be removed by washing, including washing resin on a filter, or flushing a packed bed of resin with solvent. Solid phase peptide synthesis is now a standard technology for laboratory and commercial syntheses. The synthesis of oligonucleotides has followed a similar technological development to peptides, as described by Sanghvi, Y S, Org Proc Res & Dev 4 (2000) 168-169 and relies on solid phase synthesis in which a first oligonucleotide is linked to a solid phase. Further oligonucleotides are attached via cycles of coupling and deprotection reactions, with purification between the reactions carried out by washing, including washing a resin on a filter, or flushing a packed bed of resin with solvent.

Membrane processes are well known in the art of separation science, and can be applied to a range of separations of species of varying molecular weights in liquid and gas phases (see for example "Membrane Technology" in Kirk Othmer Encyclopedia of Chemical Technology, 4$^{th}$ Edition 1993, Vol 16, pages 135-193). Nanofiltration is a membrane process utilising membranes whose pores are in the range 0.5 to 5 nm, and which have MW cutoffs of 200-3,000 Daltons. Nanofiltration has been widely applied to filtration of aqueous fluids, but due to a lack of suitable solvent stable membranes has not been widely applied to separation of solutes in organic solvents. Ultrafiltration membranes typically have MW cutoffs in the range 1,000 to 500,000 Daltons. Recently new classes of membranes have been developed which are stable in even the most difficult solvents as reported in P. Vandezande, L. E. M. Gevers and I. F. J. Vankelecom *Chem. Soc. Rev.*, (2008), Vol 37, pages 365-405. These may be polymeric membranes or ceramic membranes, or mixed matrix inorganic/organic membranes.

Diafiltration is a liquid filtration process in which a feed liquid containing at least two solutes is in contact with a membrane and is pressurised so that some fraction of the liquid passes through the membrane, wherein at least one solute has a higher rejection on the membrane than at least one other solute. Additional liquid is fed to the pressurised side of the membrane to make up for the liquid permeating through the membrane. The ratios between the concentration of the more highly retained solute and the concentration of the less retained solute in the permeate and retentate varies dynamically, increasing in the retentate and decreasing in the permeate.

The application of membrane separation to peptide synthesis has been reported for the re-concentration of peptides produced by biosynthesis as described by Tsuru T, Nakao S, Kimura S, Shutou T, *Sep. Sci. and Technol.*, Volume 29, (1994), pages 971-984 or amino acid recovery from aqueous solutions as reported in Li S, Li C, Lui Y, et al., *J. Mem. Sci.*, Volume 222 (2003), pages 191-201 or Wang X, Ying A, Wang W, *J. Mem. Sci.*, Volume 196 (2002) pages 59-67. The use of membranes during peptide synthesis to separate growing peptides from excess reagents and reaction by-products was reported in U.S. Pat. No. 3,772,264. Peptides were synthesised in a liquid phase, with poly(ethylene glycol) (PEG) as a molecular anchoring group, and separation of the growing peptide chain from impurities was achieved with aqueous phase ultrafiltration. The separation required evaporation of the organic solvent after each coupling step, neutralisation followed by evaporation after each deprotection, and then for either coupling or deprotection, water uptake before ultrafiltration from an aqueous solution. Water was then removed by evaporation and/or azeotropic distillation before re-dissolving the PEG anchored peptide back into organic solvent for the next coupling or deprotection step. The complexity of the process makes it undesirable from a commercial perspective.

SUMMARY OF THE INVENTION

According to the present invention, there is provided a process for the preparation of a first compound selected from peptides, oligonucleotides, and peptide nucleic acids; the process comprising:
(i) synthesising the first compound; and
(ii) separating the first compound formed in step (i) from a second compound, which is a reaction by-product of the synthesis of the first compound and/or an excess of a reagent used for the synthesis of a first compound, wherein the first and second compounds are dissolved in an organic solvent and are separated by a process of diafiltration using a membrane that is stable in the organic solvent and which provides a rejection for the first compound which is greater than the rejection for the second compound.

The invention further provides a process for the separation of a first compound from a second compound in an organic solvent, wherein:
(i) the first and second compounds are both dissolved in the organic solvent;
(ii) the first compound is selected from the group consisting of peptides, oligonucleotides and peptide nucleic acids; and
(iii) the second compound is a by-product of a reaction forming the first compound and/or a reagent used in said reaction;
wherein the separation is by a process of diafiltration using a membrane that is stable in the organic solvent and which provides a rejection for the first compound which is greater than the rejection for the second compound.

DESCRIPTION OF VARIOUS EMBODIMENTS

Figure 1:
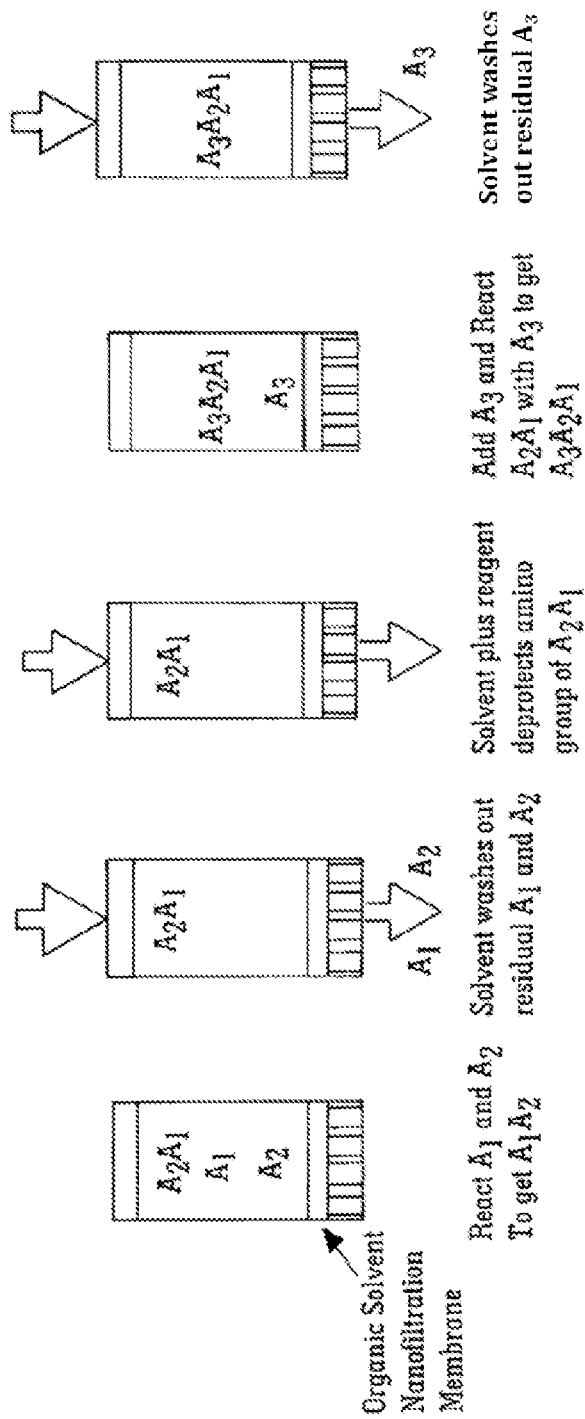
FIG. 1 shows the general approach to the synthesis of a peptide, oligonucleotide or peptide nucleic acid (collectively referred to in the Figures as "tides") from repeat units of A1, A2 and A3.

The term "peptide" used herein additionally encompasses peptide derivatives. Examples of peptide derivatives are peptides which comprise one or more synthetic or chemically modified amino acids, one or more protecting groups or a terminal group located at one or both ends of the peptide chain.

In an embodiment of the invention, a peptide comprises less than 200 amino acid residues. In a particular embodiment of the invention, a peptide comprises less than 100 amino acid residues. In a further embodiment of the invention, a peptide comprises less than 50 amino acid residues.

The term "oligonucleotide" used herein additionally encompasses oligonucleotide derivatives, for example oligonucleotides which comprise one or more synthetic or chemically modified oligonucleotides, one or more protecting groups, or one or more terminal groups located at the termini of the oligonucleotide chain.

The term "peptide nucleic acid" or "PNA" as used herein additionally encompasses peptide nucleic acid derivatives, for example peptide nucleic acids comprising one or more chemically modified purine or pyrimidine bases, one or more protecting groups, or one or more terminal groups located at the termini of the peptide nucleic acid chain.

In accordance with the invention, the first compound is separated from the second compound by diafiltration. Diafiltration can be performed in two operating modes. The first operating mode is constant volume diafiltration in which fresh solvent is fed into the filtration system at the same rate as permeate is discharged from the system, thereby maintaining constant volume in the system. The second operating mode is variable volume diafiltration in which the filtration volume is reduced by discharging permeate from the system and periodically fresh solvent is added to the system to increase the system volume before additional permeate is discharged.

Suitably, the first compound has a molecular weight greater than 200 daltons. In a particular embodiment of the invention, the first compound has a molecular weight greater than 300 daltons. In a preferred embodiment of the invention, the first compound has a molecular weight greater than 500 daltons The second compound is either a by-product of the synthesis reaction forming the first compound or a reagent used in said reaction. Any suitable method of synthesising the first compound that is known in the art may be utilised. The synthesis reaction may be a coupling or deprotection reaction. Suitably, the synthesis is carried out in a liquid phase. In particular, the synthesis may be performed in the presence of an organic solvent, which may be the same or different to the organic solvent used for the diafiltration.

In an embodiment, the process comprises modifying the first compound subsequent to separation. For example, the first compound may be modified by performing one or more additional coupling and/or deprotection steps. The modified compound may subsequently be purified, in particular using the diafiltration process of the present invention. In an embodiment, a process of the invention comprises a plurality of sequential coupling, deprotection and separation steps, thereby facilitating the synthesis of a variety of peptides, oligonucleotides and peptide nucleic acids.

Suitable membranes for use in the invention include polymeric and ceramic membranes, and mixed polymeric/inorganic membranes. Membrane rejection $R_i$ is a common term known by those skilled in the art and is defined as:

$$R_i = \left(1 - \frac{C_{P,i}}{C_{R,i}}\right) \times 100\% \qquad (1)$$

where $C_{P,i}$=concentration of species i in the permeate, permeate being the liquid which has passed through the membrane, and $C_{R,i}$=concentration of species i in the retentate, retentate being the liquid which has not passed through the membrane. It will be appreciated that a membrane is suitable for the invention if R(first compound)>R(second compound).

The membrane of the present invention may be formed from any polymeric or ceramic material which provides a separating layer capable of preferentially separating the tide from at least one reaction by-product or reagent. Preferably the membrane is formed from or comprises a material selected from polymeric materials suitable for fabricating microfiltration, ultrafiltration, nanofiltration or reverse osmosis membranes, including polyethylene, polypropylene, polytetrafluoroethylene (PTFE), polyvinylidene difluoride (PVDF), polysulfone, polyethersulfone, polyacrylonitrile, polyamide, polyimide, polyetherimide, cellulose acetate, polyaniline, polypyrrole and mixtures thereof. The membranes can be made by any technique known to the art, including sintering, stretching, track etching, template leaching, interfacial polymerisation or phase inversion. More preferably, membranes may be crosslinked or treated so as to improve their stability in the reaction solvents. Of particular mention are the membranes described in WO 2007/125367, the contents of which are incorporated herein by reference.

In an embodiment the membrane is a composite material comprising a support and a thin selectively permeable layer, and the non-porous, selectively permeable layer thereof is formed from or comprises a material selected from modified polysiloxane based elastomers including polydimethylsiloxane (PDMS) based elastomers, ethylene-propylene diene (EPDM) based elastomers, polynorbornene based elastomers, polyoctenamer based elastomers, polyurethane based elastomers, butadiene and nitrile butadiene rubber based elastomers, natural rubber, butyl rubber based elastomers, polychloroprene (Neoprene) based elastomers, epichlorohydrin elastomers, polyacrylate elastomers, polyethylene, polypropylene, polytetrafluoroethylene (PTFE), polyvinylidene difluoride (PVDF) based elastomers, polyetherblock amides (PEBAX), polyurethane elastomers, crosslinked polyether, polyamide, polyaniline, polypyrrole, and mixtures thereof.

In another embodiment, the membrane is prepared from an inorganic material such as by way of non-limiting example silicon carbide, silicon oxide, zirconium oxide, titanium oxide, or zeolites, using any technique known to those skilled in the art such as sintering, leaching or sol-gel processing. The inorganic membranes provided by Inopor GmbH (Germany) are preferred for use in this invention.

In a further embodiment, the membrane comprises a polymer membrane with dispersed organic or inorganic matrices in the form of powdered solids present at amounts up to 20 wt % of the polymer membrane. Carbon molecular sieve matrices can be prepared by pyrolysis of any suitable material as described in U.S. Pat. No. 6,585,802. Zeolites as described in U.S. Pat. No. 6,755,900 may also be used as an inorganic matrix. Metal oxides, such as titanium dioxide, zinc oxide and silicon dioxide may be used, for example the materials available from Degussa AG (Germany) under their Aerosol and AdNano trademarks. Mixed metal oxides such as mixtures of cerium, zirconium, and magnesium oxides may be used. Preferred matrices will be particles less than 1.0 micron in diameter, preferably less than 0.1 microns in diameter, and preferably less than 0.01 microns in diameter.

The first compound may be attached via a suitable chemistry to a support, e.g. a polymer, dedrimer, dendron, hyperbranched polymer or inorganic or organic nanoparticle, which acts as a soluble molecular anchor that allows the first compound to stay in solution during the reaction and diafiltration stages of the invention, and provides an increased molecular bulk to enhance membrane rejection. Suitable polymers for use as molecular anchors include polycondensation matrices or polymerisation matrices containing heteroatom functions. These heteroatom functions can contain oxygen, nitrogen, or can contain more than one heteroatom, such as acid amide groups. Examples of polymers used in the present invention include polyalkylene glycols including polyethylene glycol, polycaprolactone, polyethylene glycol esterified with citric acid, copolymers of polyethyleneglycol and succinic acid, of vinylpyrrolidone and acrylic acid or b-hydroxy-ethylacrylate; or of acrylamide and vinylactetate. Suitable dendrimers for use in the present invention include poly(amidoamine), also known as PAMAM dendrimers; phosphorous dendrimers; polylysine dendrimers; and polypropylenimine (PPI) dendrimers which can have surface functional groups including —OH, —NH$_2$, —PEG, and COOH groups. Nanoparticles may be obtained from commercial sources or synthesised in-situ to provide controlled dimensions, and suitable nanoparticles may be from $SiO_2$, $TiO_2$, or other organic or inorganic materials. U.S. Pat. No. 3,772,264 reports suitable chemistries for linking amino acids and peptides to molecular anchors. Bonora et al *Bioconjugate Chem.*, (1997) Volume 8 (6), pages 793-797, describes chemistries for linking nucleotides and oligonucleotides to molecular anchors. Christensen et al. *J. Pept. Sci.* (1995) May-June; 1(3):pages 175-83 describe suitable techniques for linking peptide nucleic acids to molecular anchors. The removal of the first compound from the support can be readily accomplished using techniques well known to those skilled in the art, for example those reported in U.S. Pat. No. 3,772,264.

Suitable chemistries for coupling and deprotection reactions of peptides are well known to those skilled in the art, for example see Amino Acid and Peptide Synthesis, $2^{nd}$ Edn, J Jones, Oxford University Press 2002, or Schroder-Lubbke, The Peptides, New York 1967. Suitable chemistries for coupling and deprotection reactions on oligonucloetides are well known to those skilled in the art, for example see P. S. Millar, *Bioconjugate Chemistry*, (1990), Volume 1, pages 187-191 and C. B. Reese *Org. Biomol. Chem*. (2005) Volume 3 pages 3851-3868. Suitable chemistries for coupling and deprotection reactions of peptide nucleic acids are known to those skilled in the art, for example see B. Hyrup and P. E. Nielsen *Bioorganic & Medicinal Chemistry* (1996), Volume 4, Issue 1, Pages 5-23.

The term "organic solvent" will be well understood by the average skilled reader and includes, for example, an organic liquid with molecular weight less than 300 Daltons. It is understood that the term solvent also includes a mixture of solvents.

By way of non-limiting example, solvents include aromatics, alkanes, ketones, glycols, chlorinated solvents, esters, ethers, amines, nitriles, aldehydes, phenols, amides, carboxylic acids, alcohols, furans, and dipolar aprotic solvents, and mixtures thereof and with water.

By way of non-limiting example, specific examples of solvents include toluene, xylene, benzene, styrene, anisole, chlorobenzene, dichlorobenzene, chloroform, dichloromethane, dichloroethane, methyl acetate, ethyl acetate, butyl acetate, methyl ether ketone (MEK), methyl iso butyl ketone (MIBK), acetone, ethylene glycols, ethanol, methanol, propanol, butanol, hexane, cyclohexane, dimethoxyethane, methyl tert butyl ether (MTBE), diethyl ether, adiponitrile, N,N dimethylformamide, dimethylsulfoxide, N,N dimethylacetamide, dioxane, nitromethane, nitrobenzene, pyridine, carbon disulfide, tetrahydrofuran, methyl-tetrahydrofuran, N-methylpyrrolidone, N-ethyl pyrrolidone, acetonitrile, and mixtures thereof and with water.

Synthesis Scheme and Apparatus

Figure 2:
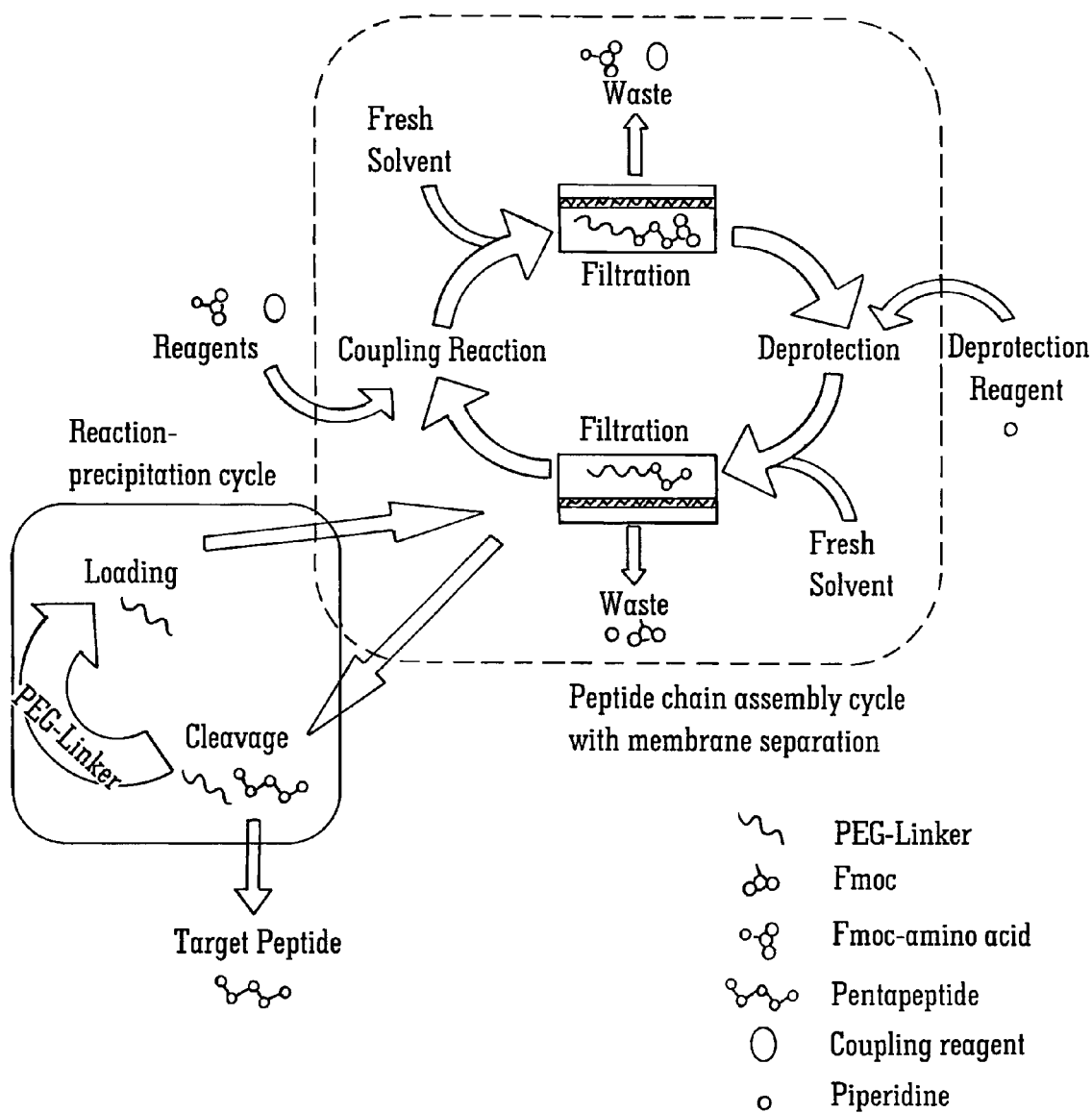
FIG. 2 shows schematic representation of the membrane enhanced peptide synthesis.
Figure 3:
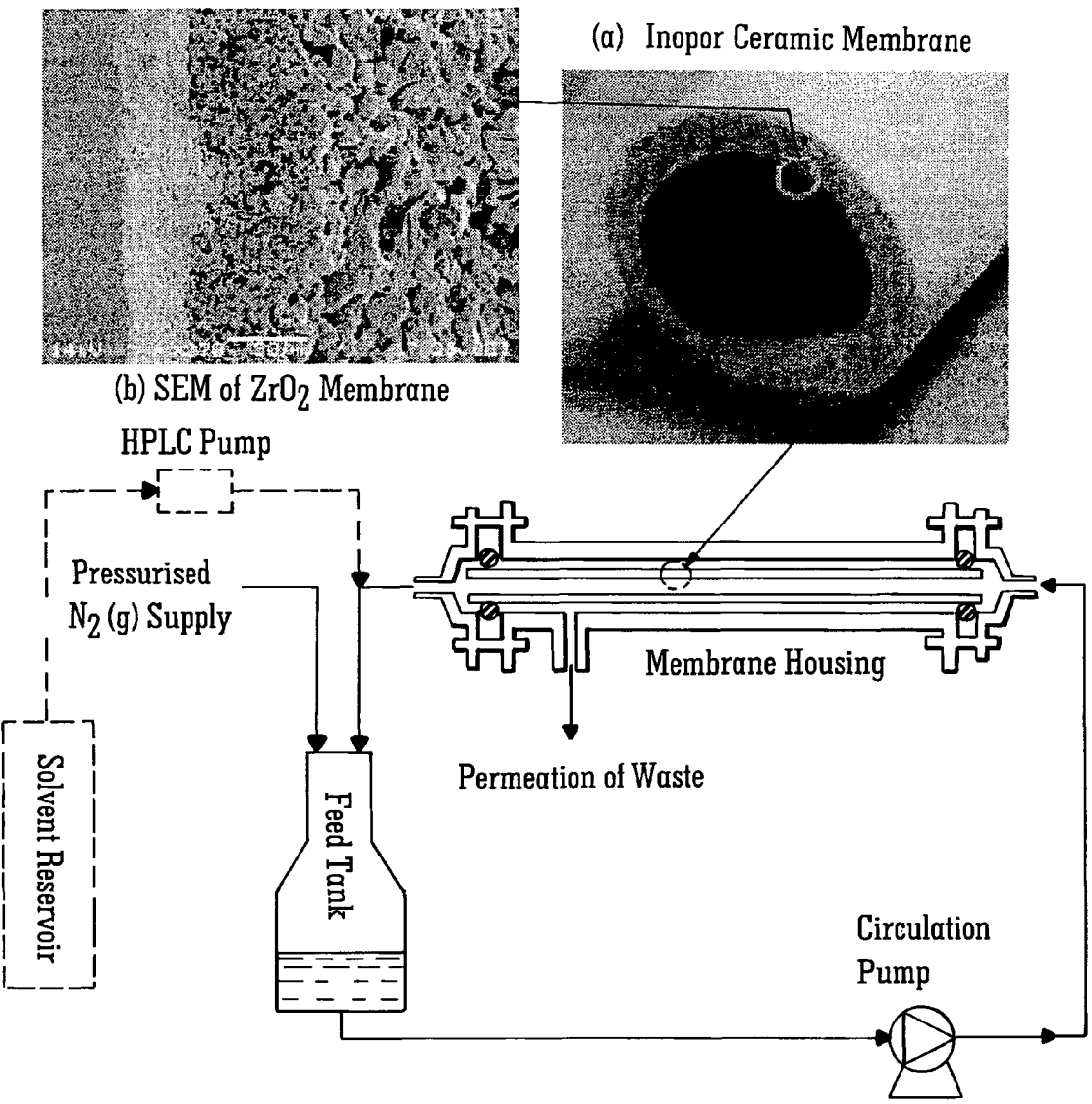
FIG. 3 shows the equipment used in the membrane enhanced peptide synthesis described in Examples 2 and 3, and in the oligonucleotide synthesis described in Example 4, including expanded images of (a) the Inopor Ceramic Membrane, and (b) the SEM of Zr02 Membrane.

Examples 1 to 3 illustrate the synthesis of pentapeptides. The scheme employed is shown in FIG. 2. The apparatus employed is shown in FIG. 3. The apparatus was used both to carry out rejection tests, and to perform syntheses. Both coupling and deprotection steps are performed in the Reaction Vessel (Feed Tank) at atmospheric pressure. The Circulation Pump recirculates the reaction solution through the membrane cartridge and ensures good liquid mixing throughout. Upon completion of each reaction, the system is pressurised using $N_2$ to ~7 barg. The resulting solvent flow permeating through the membrane is balanced by a constant flow of fresh solvent (DMF) supplied to the Reaction Vessel (Feed Tank) from the Solvent Reservoir via an HPLC pump. The same procedure is applied at each reaction/washing cycle. The peptides were assembled on a soluble polymeric molecular anchor to increase retention by the membrane. PEG was chosen as the polymeric support.

The following abbreviations are used in the Examples:

Di-chloromethane DCM
Diisopropylcarbodiimide DIC
Diisopropylethylamine DIPEA
Dimthylformamide DMF
N-α-Fmoc-L-Alanine Fmoc-Ala
N-α-Fmoc-bis-t-butoxycarbonyl-L-arginine Fmoc-Arg (Boc)$_2$
N-α-Fmoc-L-aspartic acid β-t-butyl ester Fmoc-Asp (O$^t$Bu)
N-α-Fmoc-N-t-Boc-L-lysine Fmoc-Lys(Boc)
N-α-Fmoc-O-t-butyl-L-tyrosine Fmoc-Tyr($^t$Bu)
N-α-Fmoc-L-valine Fmoc-Val
4-Hydroxymethylphenoxyacetic acid HMPA
N-Hydroxybenzotriazole HOBt
Benzotriazole-1-yl-oxy-tris-pyrrolidino-phosphonium hexafluorophosphate PyBOP
Acetonitrile MeCN
Triethylamine TEA
4-dimethylaminopyridine DMAP
Chloroform CHCl$_3$
Methanol MeOH
N-methylimidazole NMI
Ethyl acetate EtOAC
Dichloroacetic acid DCA
Pyridinium trifluoroacetate PyTFA
tert-butyl hydroperoxide TBHP

EXAMPLE 1

A model peptide with sequence Tyr-Ala-Tyr-Ala-Tyr (SEQ ID NO 1) was produced by membrane enhanced peptide synthesis (MEPS) using a polymeric membrane. The sequence was chosen in order to include one of the largest common protected amino acids Fmoc-Tyr($^t$Bu) and one of the smallest protected hydrophobic amino acids, Fmoc-Ala. A chemically cross-linked polyimide membrane (DuraMem™, MET Ltd, UK believed to be made following techniques described in PCT/GB2007/050218) was used to perform the membrane separation steps. The rejection of the MeO-PEG-lnker-peptide was ~100% for the coupling step and >99.7% for the deprotection step.

Methylated Amino Poly(ethylene glycol) (MeO-PEG-NH$_2$) Synthesis

The procedure used to produce MeO-PEG-NH$_2$ is illustrated in Scheme 1:

Scheme 1: Methylated amino PEG synthesis

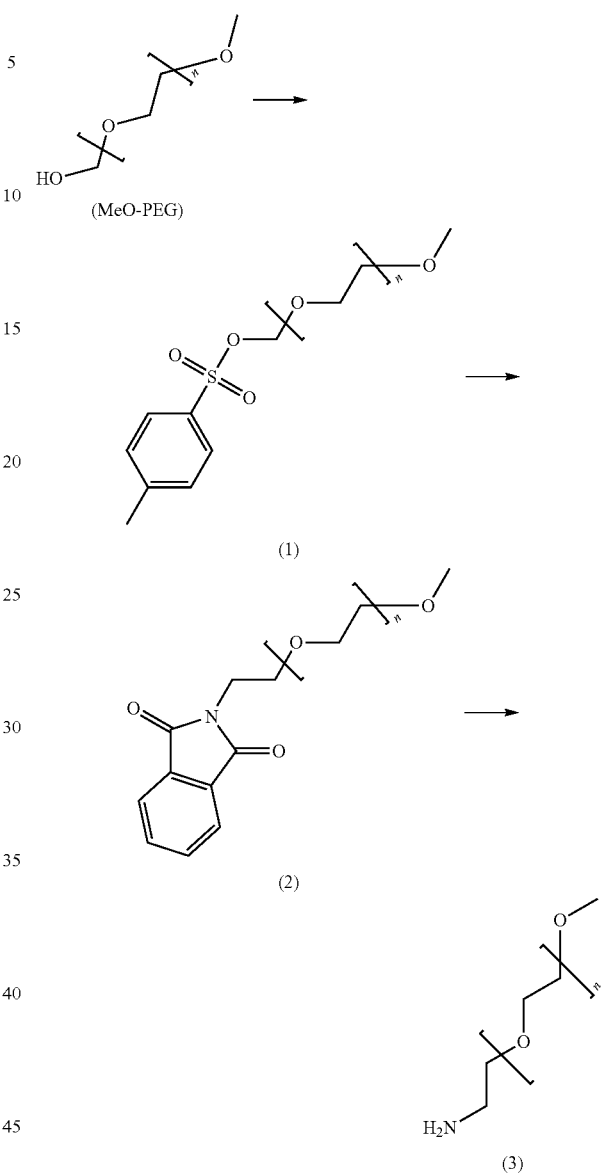

MeO-PEG-Tosylate synthesis (1). 20 g of Polyethylene glycol monomethyl ether (MeO-PEG, MW-5000 gmol$^{-1}$) was dehydrated in vacuo at 80° C. for 4 hours before dissolving in 100 ml of DCM (25 mL per mmol MeO-PEG). 36 g of p-toluenesulfonyl chloride (46 mmol per mmol MeO-PEG) and 6 ml of pyridine (1.5 mL per mmol PEG) were added to the PEG solution, and the reaction was performed under nitrogen atmosphere and continuous stirring for 12 hours. The resulting solution was concentrated in vacuo and product (MeO-PEG-Tos) was precipitated by adding diethyl ether and kept at 4° C. for few hours to complete precipitation. The precipitate was filtered and washed with ether, recrystallised with ethanol and dried in vacuo. UV analysis was performed by measuring the absorption at 270 nm to verify the presence of the tosylate group.

MeO-PEG-Phthalimide synthesis (2). 18 g of MeO-PEG-Tos and 8 g of potassium phthalimide (10 mmol per mmol MeO-PEG-Tos) were dissolved in 50 ml DMF (14 mL per mmol MeO-PEG-Tos), and heated under reflux and nitrogen atmosphere for 4 hours. Solid residuals were filtered, and diethyl ether was added into filtrate to precipitate product out of solution. The solution was kept at 4° C. for 5 hours to complete the precipitation. The product was filtered and washed with ether, followed by digestion with 50 ml of DCM. The insoluble impurities were filtered and MeO-PEG-Phth was precipitated from filtrate with ether. The product was filtered again, washed with ether and dried in vacuo. The appearance of the phthalimide group was verified by UV analysis at 292 nm and 264 nm.

MeO-Amino-PEG synthesis (3). 16 g of MeO-PEG-Phth and 8 ml of hydrazine hydrate (40 mmol per mmol MeO-PEG-Phth) were dissolved in 60 ml of ethanol (18.5 mL per mmol MeO-PEG-Phth) and heated under reflux for 12 hours. The product mixture was cooled to room temperature before precipitation with diethyl ether. The precipitate was filtered and re-dissolved in 30 ml of DCM, the insoluble impurities were filtered and MeO-PEG-$NH_2$ product was precipitated from the filtrate, washed with diethyl ether, recrystallised with ethanol and finally dried in vacuo. The product was analysed with UV analysis for disappearance of the phthalimide group and the Kaiser test applied to verify the presence of the amino group. The conversion (~80%) was determined by titration with $HCl_{(aq)}$.

Peptide Synthesis

Synthesis of MeO-PEG-HMPA. 1 g of MeO-PEG-$NH_2$ (3) was dissolved in 4 ml of DCM. 0.073 g of HMPA, 0.21 g of PyBOP (both 2 mol per mol MeO-PEG-$NH_2$) and 0.0026 g of DIPEA (0.1 mol per mol MeO-PEG-$NH_2$) were pre-activated in 4 ml of DMF for 15 minutes before being added into the PEG solution. The product was precipitated with diethyl ether at 4° C. for 2 hours and separated by centrifugation, followed by ether washes. The crude product was purified by recrystallisation with ethanol. MeO-PEG-HMPA product was dried under vacuum and analysed by $H^1$-NMR analysis. Conversion was estimated based on the ratio between peaks at 3.4 (s, 3H) for MeO-group and 6.7 (d, 2H), 6.9 (d, 2H) for aromatic system on HMPA linker.

Synthesis of Fmoc-Tyr-HMPA-PEG-OMe. 0.5 g of MeO-PEG-HMPA was pre-dissolved in 4 ml of DMF (45 L per mol MeO-PEG-HMPA). 0.096 g of Fmoc protected Tyr (Fmoc-Tyr($^t$Bu)), 0.028 g of HOBt, 0.026 g of DIC (all 2 mol per mol MeO-PEG-HMPA) and 0.0013 g of DIPEA (0.1 mol per mol MeO-PEG-HMPA) were pre-activated for 15 minutes in 4 ml of DMF (10 L per mol MeO-PEG-HMPA) before being mixed with MeO-PEG-HMPA solution for 2 hours. Upon reaction completion the excess reagents were removed by diafiltration (40× starting volume) with chemically cross-linked polyimide membrane. Permeate samples were collected to monitor PEG-anchored-peptide loses and to verify the removal of impurities. Small retentate samples were collected and precipitated for $H^1$-NMR analysis to estimate the conversion and for Kaiser tests to confirm the absence of the amino group.

Chain assembly with Fmoc-amino acids. 0.046 g of Fmoc-Ala was pre-activated with 0.076 g of PyBOP, 0.020 g of HOBt (all 2 mol per mol MeO-PEG-HMPA) and 0.001 g of DIPEA (0.1 mol per mol MeO-PEG-HMPA) in 4 ml of DMF (10 L per mol MeO-PEG-HMPA) for 15 minutes. A separate solution of MeO-PEG-HMPA-Tyr-H in DMF was prepared and mixed with the pre-activated solution. The resulting solution was mixed vigorously for 1 hour followed by diafiltration washes (40× starting volume) with a chemically cross-linked polyimide membrane. Similar procedures were applied to the attachment of further amino-acids.

Fmoc-deprotection. 20% piperidine/DMF solution was prepared by adding the required amount of pure piperidine to the known solution volume. Deprotection was performed for 30 minutes. Separation after the deprotection was performed via diafiltration (40× starting volume) with chemically cross-linked polyimide membrane.

Side chain deprotection and cleavage reaction. The solution containing 0.33 g of PEG-peptide building block was removed from the filtration cell, the product precipitated with diethyl ether and dried in vacuo. The precipitate was then re-dissolved into 20 ml per mmol of acidolysis solution for 3 hours. Diethyl ether was used to precipitate the target peptide together with MeO-PEG-HMPA.

Peptide Purity

Figure 4:
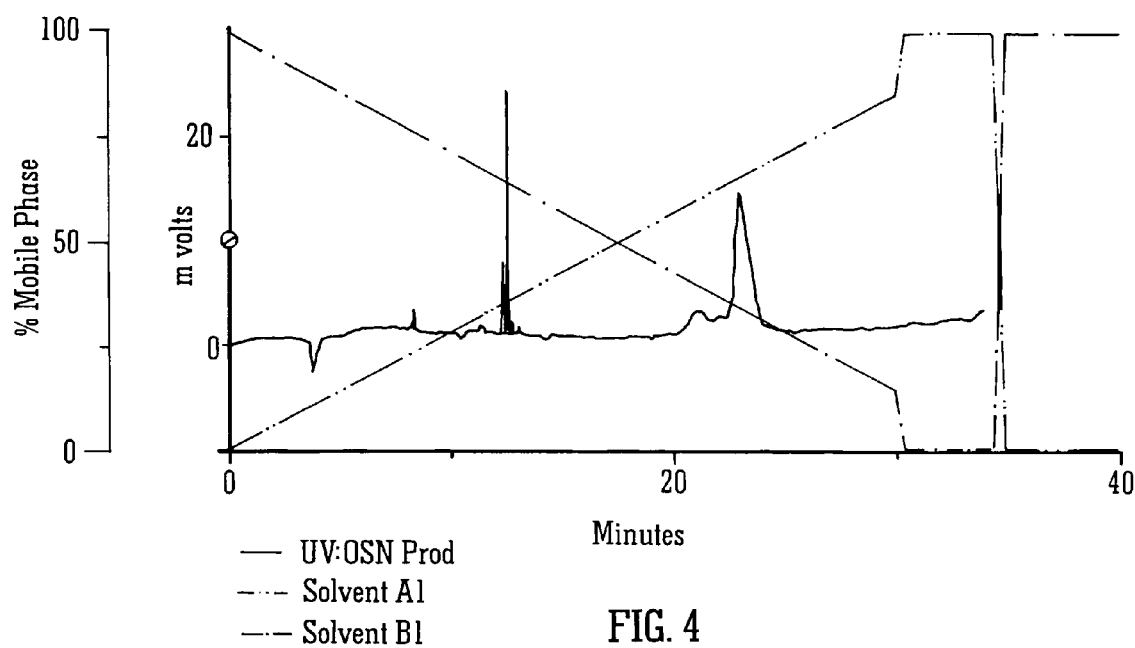
FIG. 4 shows HPLC chromatography data for SEQ ID NO 1, the pentapeptide produced in Example 1.
Figure 5:
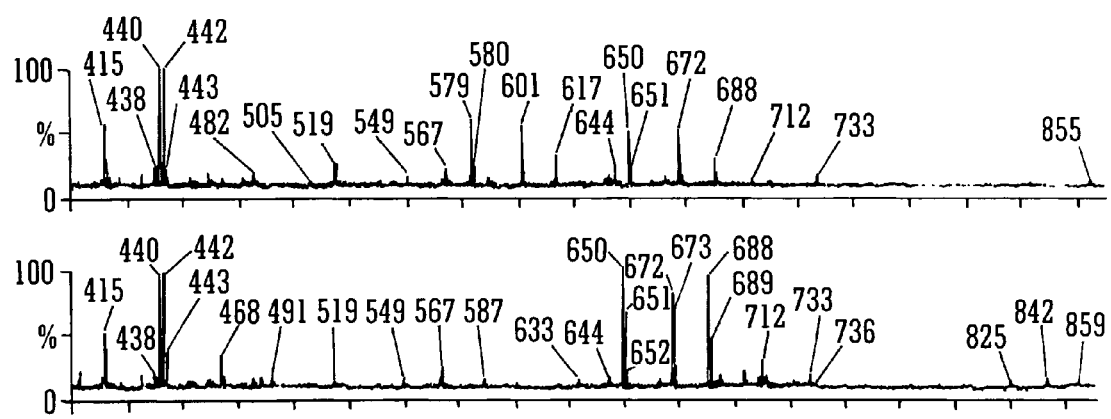
FIG. 5 shows MALDI-TOF mass spectra for SEQ ID NO 1, the pentapeptide produced in Example 1.

FIGS. 4 and 5 show data for HPLC and MALDI-TOF analysis of the purity of the resulting pentapeptide. No random sequences were generated from the synthesis showing that most of the un-reacted reagents and impurities were removed from the system before attachment was performed. The only by-products from deletion sequences were due to incomplete reaction and not related to the separation procedure.

EXAMPLE 2

The model peptide sequence Tyr-Ala-Tyr-Ala-Tyr (SEQ ID NO 1) was produced again as an example of membrane enhanced peptide synthesis with a ceramic membrane. An Inopor zirconium oxide coated membrane with 3 nm pore size and hydrophobic surface modification (Inopor GmbH, Germany) was used in this example.

The membrane rejection of the MeO-PEG-peptide increased to >99.7% after the first and the second amino acid attachment and ~100% for later attachments.

Methylated Amino Poly(ethylene glycol)(MeO-PEG-$NH_2$) Synthesis

The MeO-PEG-$NH_2$ used in this example was produced by the same route as described in Example 1.

Membrane Relection Results

Rejection data for this membrane are presented in Table 1. The Inopor membrane exhibited 99% rejection of both MeO-PEG and MeO-PEG-HMPA.

A number of Fmoc-amino acids were tested covering a wide range of properties—the lowest MW amino acid and the highest MW amino acid, acidic, basic and hydrophobic amino acids, and some of the amino acids most frequently occurring in proteins. Further rejection tests on coupling activators and reagents were performed. Results showed that PyBOP and HBTU activators exhibit relatively high rejection by the membrane, presumably due to the fact that these activators are bulky salts so both steric hindrance and Donnan effects would contribute to their retention. Nevertheless, during the coupling reaction these activators break down into smaller molecules hence the final rejection is expected to be lower. The coupling reagent DIC showed very low rejection of 13%, similarly piperidine, the deprotection reagent for the Fmoc-deprotection was rejected only 5%. DIC however can only be used in combination with HOBt for suppressing racemization, and so it is important to examine the rejection of HOBt. There are two types of HOBt available on the market, one is crystalline flake HOBt, the other is a wet powder HOBt.$H_2O$, and as shown in Table 1 the moisture content seems to affect the rejection of HOBt by the membrane. The use of PyBOP or HBTU does not require addition of HOBt and the rejection of HOBt that breaks off from these activators during the coupling reaction is expected to be low, since it is free of moisture. Finally the rejection of HMPA linker was also investigated. The rejection of HMPA is relatively low (39%) with 99% rejection of MeO-PEG-HMPA.

TABLE 1

Rejection data for PEGs, protected amino acids and other common reagents used in peptide synthesis obtained with Inopor $ZrO_2/Al_2O_3$ ceramic membrane. The experiments were performed in a batch mode, and the rejection was determined according to Eq. 1.

| Compound | MW [g·mol$^{-1}$] | | Inopor $ZrO_2/Al_2O_3$ Membrane Rejection [%] | Error* [%] | Flux [Lm$^{-2}$h$^{-1}$] |
|---|---|---|---|---|---|
| Fmoc-Ala-OH | 311 | Amino acid | 55 | 7.3 | 27 |
| Fmoc-Arg (Boc)$_2$—OH | 597 | Amino acid | 68 | 8.7 | 26 |
| Fmoc-Asp (O$^t$Bu)—OH | 412 | Amino acid | 41 | 9.2 | 27 |
| Fmoc-Cys ($^t$Bu)—OH | 400 | Amino acid | 50 | 3.8 | 28 |
| Fmoc-Gly-OH | 297 | Amino acid | 51 | 13.5 | 11 |
| Fmoc-Lys (Boc)—OH | 469 | Amino acid | 59 | 8.7 | 29 |
| Fmoc-Trp (Boc)—OH | 527 | Amino acid | 61 | 3.6 | 27 |
| Fmoc-Tyr ($^t$Bu)—OH | 460 | Amino acid | 41 | 6.6 | 25 |
| Fmoc-Val-OH | 339 | Amino acid | 42 | 4.5 | 25 |
| DIC | 126 | Activator | 13 | 45.5 | 26 |
| HOBt | 135 | Racemization suppressor | 32 | 7.3 | 21 |
| HOBt•H$_2$O | 135 | Racemization suppressor | 61 | 12.4 | 22 |
| HBTU | 379 | Activator | 51 | 7.0 | 25 |
| PyBOP | 520 | Activator | 64 | 3.5 | 27 |
| HMPA | 182 | Linker | 39 | 11.4 | 26 |
| Piperidine | 85 | Deprotection reagent | 5 | 3.3 | 25 |
| MeO-PEG | 5000 | Anchor | 99 | 9.7 | 25 |
| MeO-PEG-HMPA | 5182 | Anchor | 99 | 39.8 | 20 |

*Error estimated from the mass balance between feed, permeate and retentate

Peptide Synthesis

Synthesis of MeO-PEG-HMPA. 24 g of MeO-PEG-NH$_2$ (3) was dissolved in 100 ml of DCM. 0.9 g of HMPA, 2.5 g of PyBOP (both 2 mol per mol MeO-PEG-NH$_2$) and 0.06 g of DIPEA (1 mol per mol MeO-PEG-NH$_2$) were pre-activated in 80 ml of DMF for 15 minutes before being added into the PEG solution. The product was precipitated with diethyl ether at 4° C. for 2 hours and separated by centrifugation, followed by ether washes. The crude product was purified by recrystallisation with ethanol. MeO-PEG-HMPA product was dried under vacuum and analysed by H$^1$-NMR analysis. Conversion was estimated based on the ratio between peaks at 3.4 (s, 3H) for MeO-group and 6.7 (d, 2H), 6.9 (d, 2H) for aromatic system on HMPA linker.

Synthesis of Fmoc-Tyr-HMPA-PEG-OMe. 11 g of MeO-PEG-HMPA was pre-dissolved in 60 ml of DMF (45 L per mol MeO-PEG-HMPA). 2.0 g of Fmoc protected Tyr (Fmoc-Tyr), 0.5 g of HOBt, 0.55 g of DIC (all 2 mol per mol MeO-PEG-HMPA) and 0.05 g of DIPEA (1 mol per mol MeO-PEG-HMPA) were pre-activated for 15 minutes in 50 ml of DMF (10 L per mol MeO-PEG-HMPA) before being mixed with MeO-PEG-HMPA solution for 2 hours. Upon reaction completion the excess reagents were removed by constant volume diafiltration (10× starting volume) with Inopor ceramic membrane. Permeate samples were collected for PEG-peptide loses monitoring and to verify the removal of impurities. Small retentate samples were collected and precipitated for H$^1$-NMR analysis to estimate the conversion and for application of the Kaiser test to confirm the absence of amino group.

Chain assembly with Fmoc-amino acids. 1.3 g of Fmoc-Ala was pre-activated with 2.2 g of PyBOP, 0.6 g of HOBt (all 2 mol per mol MeO-PEG-HMPA) and 0.026 g of DIPEA (1 mol per mol MeO-PEG-HMPA) in 20 ml of DMF (10 L per mol MeO-PEG-HMPA) for 15 minutes. The pre-activated solution was mixed with the solution of MeO-PEG-HMPA-Tyr-H in DMF from the previous steps. The resulting solution was mixed vigorously for 2 hours followed by diafiltration washes (10× starting volume) with the Inopor ceramic membrane. A similar procedure was applied for the attachment of further amino-acids.

Fmoc-deprotection. 20% piperidine/DMF solution was prepared by adding the required amount of piperidine to the known solution volume. Deprotection was performed for 30 minutes. Purification after deprotection was performed via diafiltration (12× starting volume) with the Inopor ceramic membrane.

Side chain deprotection and cleavage reaction. The solution containing 5.5 g of PEG-peptide building block was removed from the filtration cell, the product precipitated with diethyl ether and dried in vacuo. The precipitate was then re-dissolved into 20 ml per mmol of acidolysis solution for 3 hours. Diethyl ether was used to precipitate the target peptide together with MeO-PEG-HMPA.

Peptide Purity

Figure 6:
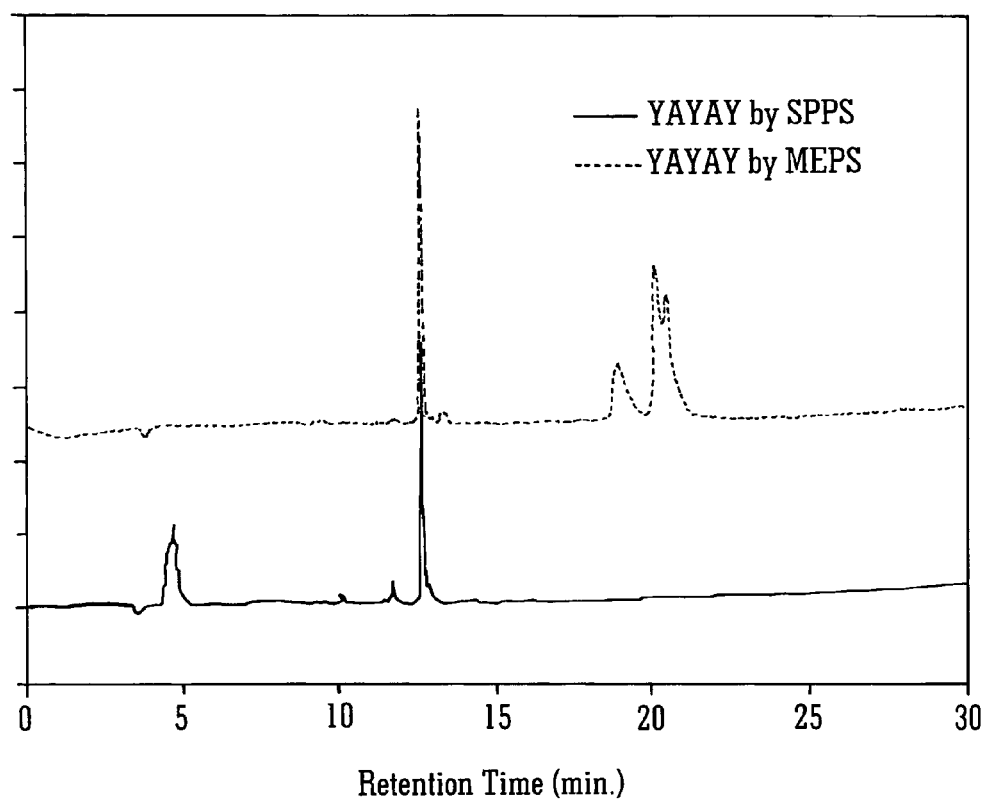
FIG. 6 shows HPLC chromatography data for SEQ ID NO 1, the pentapeptide produced in Example 2.
Figure 7:
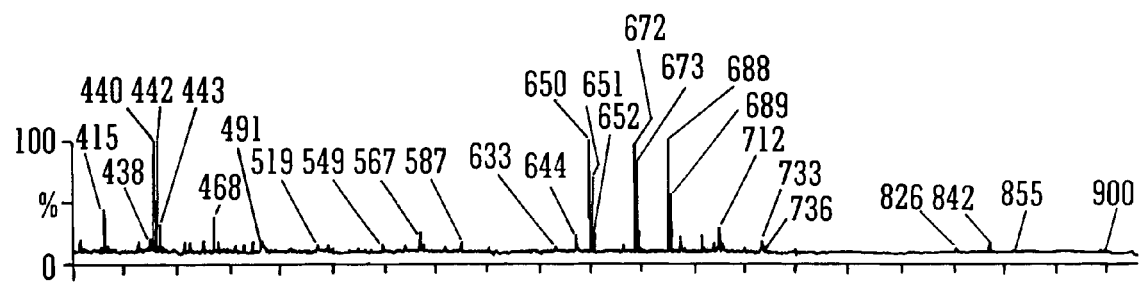
FIG. 7 shows MALDI-TOF mass spectra for SEQ ID NO 1, the pentapeptide produced in Example 2.

In this example, 2 mmol of peptide, Tyr-Ala-Tyr-Ala-Tyr (SEQ ID NO 1) was produced which yielded more than 1 g of product. The HPLC result shown in FIG. 6 indicates the purity of Tyr-Ala-Tyr-Ala-Tyr to be excellent (~100%) together with the MALDI-TOF mass spectrum shown in FIG. 7 confirming the molecular weight of the product.

EXAMPLE 3

In this example the pentapeptide Thymopentin (H-Arg-Lys-Asp-Val-Tyr-OH) SEQ ID NO 2 was made with the both the Membrane Enhanced Peptide Synthesis (MEPS) process and for comparison using the Solid Phase Peptide Synthesis (SPPS) process.

Methylated Amino Poly(ethylene glycol)(MeO-PEG-NH$_2$) Synthesis

The methylated amino poly(ethylene glycol) synthesized for this example was based on the procedure shown in Scheme 2.

13

Scheme 2: Methylated amino PEG synthesis

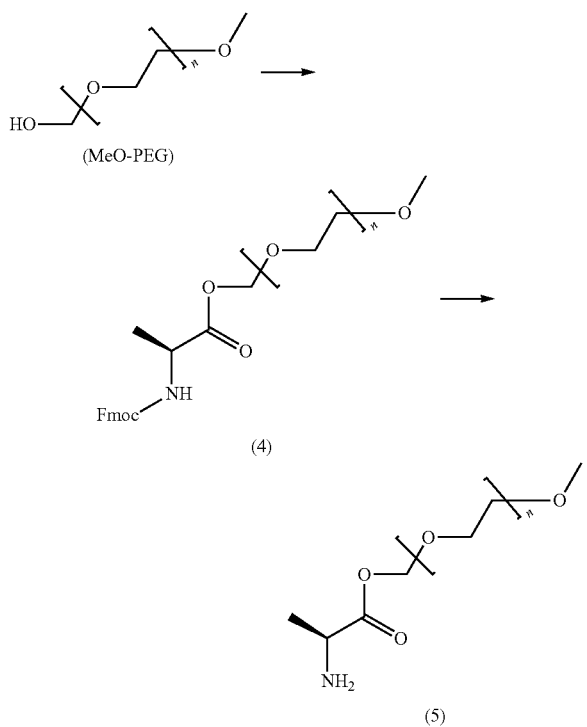

Attachment of Fmoc-Ala onto MeO-PEG (4). 10 g of MeO-PEG was dissolved in 20 ml of DCM (10 ml per mmol MeO-PEG), while 1.2 g of 0.54 g of Fmoc-Ala and HOBt (both 2 mol per mol MeO-PEG) were dissolved in 8 ml of DMF (4 ml per mmol MeO-PEG) before mixing the two solutions together. 0.25 g of DIC (2 mol per mol MeO-PEG) was afterward added and mixed vigorously for 2 hours at 4° C. Solid impurities were filtered and product was precipitated with diethyl ether and dried. The coupling step was repeated 3 times to obtain conversion >80%. MeO-PEG-Ala-Fmoc product was recrystallised first from DMF by adding diethyl ether followed by recrystallisation with ethanol. The conversion was determined with $H^1$-NMR as a ratio between the peaks at 3.4 (s, 3H) for the MeO— group and 1.4 (d, 1H) for Me- group of alanine.

Deprotection of Fmoc-group (5). Standard 20% v/v piperidine/DMF solution was used to remove Fmoc-protecting group from (4). After deprotection the product was precipitated and washed with diethyl ether, recrystallised with ethanol and dried in vacuo. $H^1$-NMR was used to verify the disappearance of Fmoc-group at 7.2 (t, 2H), 7.3 (t, 2H), 7.5 (d, 2H) and 7.7 (d, 2H). The Kaiser test was used to confirm the presence of amino functional group.

Peptide Synthesis

Synthesis of MeO-PEG-HMPA. 10 g of MeO-PEG-NH$_2$ (5) was dissolved in 50 ml of DCM. 0.72 g of HMPA, 2.1 g of PyBOP (both 2 mol per mol MeO-PEG-NH$_2$) and 0.026 g of DIPEA (1 mol per mol MeO-PEG-NH$_2$) were pre-activated in 50 ml DMF for 15 minutes before being added into the PEG solution. The product was precipitated with diethyl ether at 4° C. for 2 hours and separated by centrifugation, followed by ether washes. The crude product was purified by recrystallisation with ethanol. MeO-PEG-HMPA product was dried under vacuum and analysed by $H^1$-NMR analysis. Conversion was estimated based on the ratio between peaks at 3.4 (s, 3H) for MeO-group and 6.7 (d, 2H), 6.9 (d, 2H) for aromatic system on HMPA linker.

14

Synthesis of Fmoc-Tyr($^t$Bu)-HMPA-PEG-OMe. 10 g of MeO-PEG-HMPA was pre-dissolved in 60 ml of DMF (45 L per mol MeO-PEG-HMPA). 1.8 g of Fmoc protected Tyr (Fmoc-Tyr($^t$Bu)), 0.54 g of HOBt, 0.50 g of DIC (all 2 mol per mol MeO-PEG-HMPA) and 0.026 g of DIPEA (1 mol per mol MeO-PEG-HMPA) were pre-activated for 15 minutes in DMF (10 L per mol MeO-PEG-HMPA) before being mixed with MeO-PEG-HMPA solution for 2 hours. Upon reaction completion the excess reagents were removed by constant volume diafiltration (10× starting volume) with the Inopor ceramic membrane. Permeate samples were collected for monitoring PEG-peptide losses and to verify the removal of impurities. Small retentate samples were collected and precipitated for $H^1$-NMR analysis to estimate the conversion and for Kaiser testing to confirm the absence of the amino group.

Chain assembly with Fmoc-amino acids. 1.4 g of Fmoc-Val was pre-activated with 2.2 g of PyBOP, 0.6 g of HOBt (all 2 mol per mol MeO-PEG-HMPA) and 0.026 g of DIPEA (1 mol per mol MeO-PEG-HMPA) in DMF (10 L per mol MeO-PEG-HMPA) for 15 minutes. A separate solution of MeO-PEG-HMPA-Tyr-H in DMF was prepared and mixed with the pre-activated solution. The resulting solution was mixed vigorously for 1 hour followed by diafiltration washes (10× starting volume) with the Inopor ceramic membrane. A similar procedure was applied for the remaining Fmoc-Arg(Boc)$_2$, Fmoc-Lys(Boc) and Fmoc-Asp(O$^t$Bu) amino-acid attachments.

Fmoc-deprotection. 20% piperidine/DMF solution was prepared by adding the required amount of pure piperidine to the known solution volume. Deprotection was performed for 30 minutes. Purification after the deprotection was performed via diafiltration (12× starting volume) with the Inopor ceramic membrane.

Side chain deprotection and cleavage reaction. The solution containing 8.5 g of PEG-peptide building block was removed from the filtration cell, the product precipitated with diethyl ether and dried in vacuo. The precipitate was then re-dissolved into 20 ml per mmol of acidolysis solution for 3 hours. Diethyl ether was used to precipitate the target peptide together with MeO-PEG-HMPA.

Peptide Purity

Figure 8:
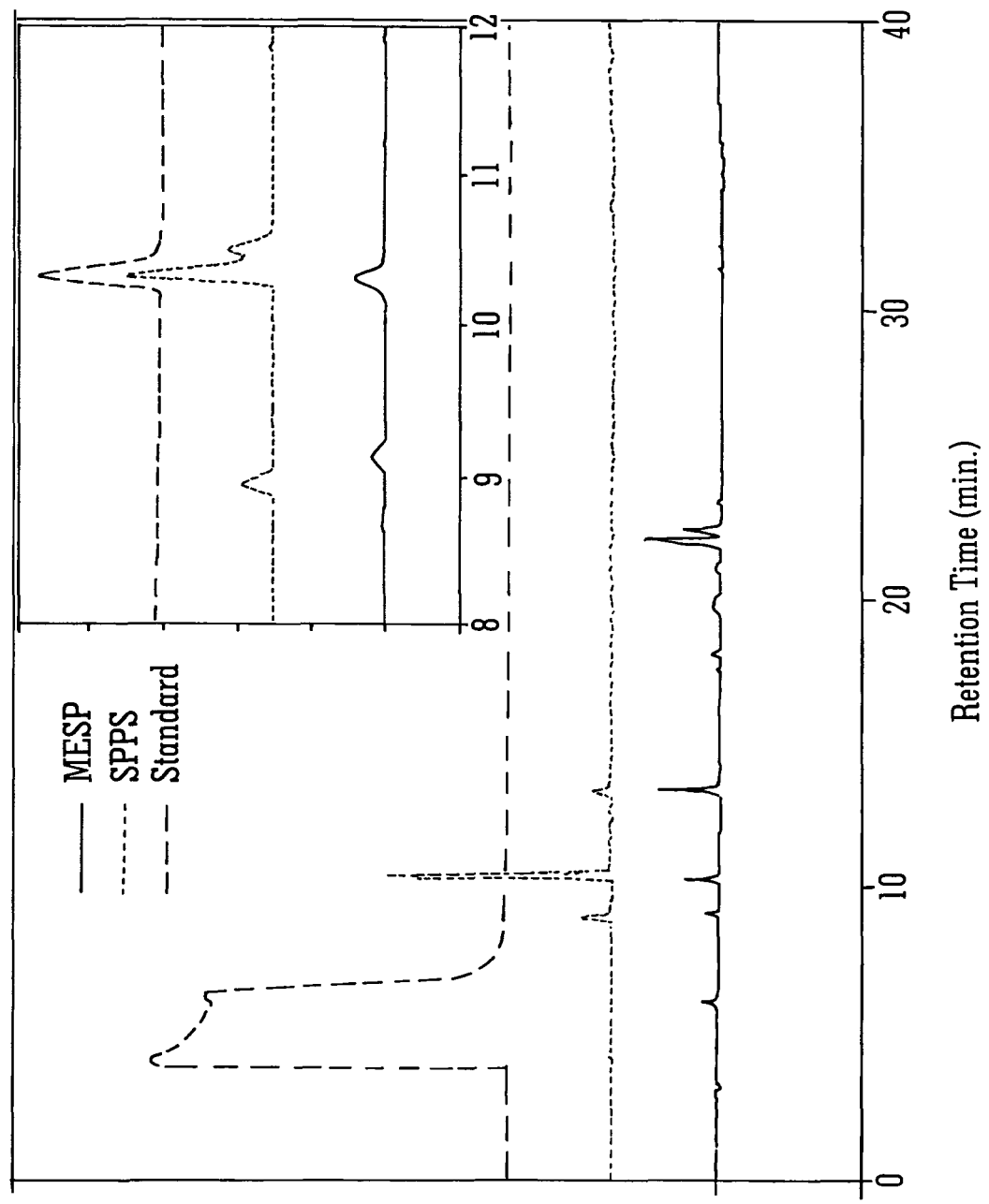
FIG. 8 shows HPLC data for SEQ ID NO 2, the pentapeptide produced in Example 3.
Figure 9:
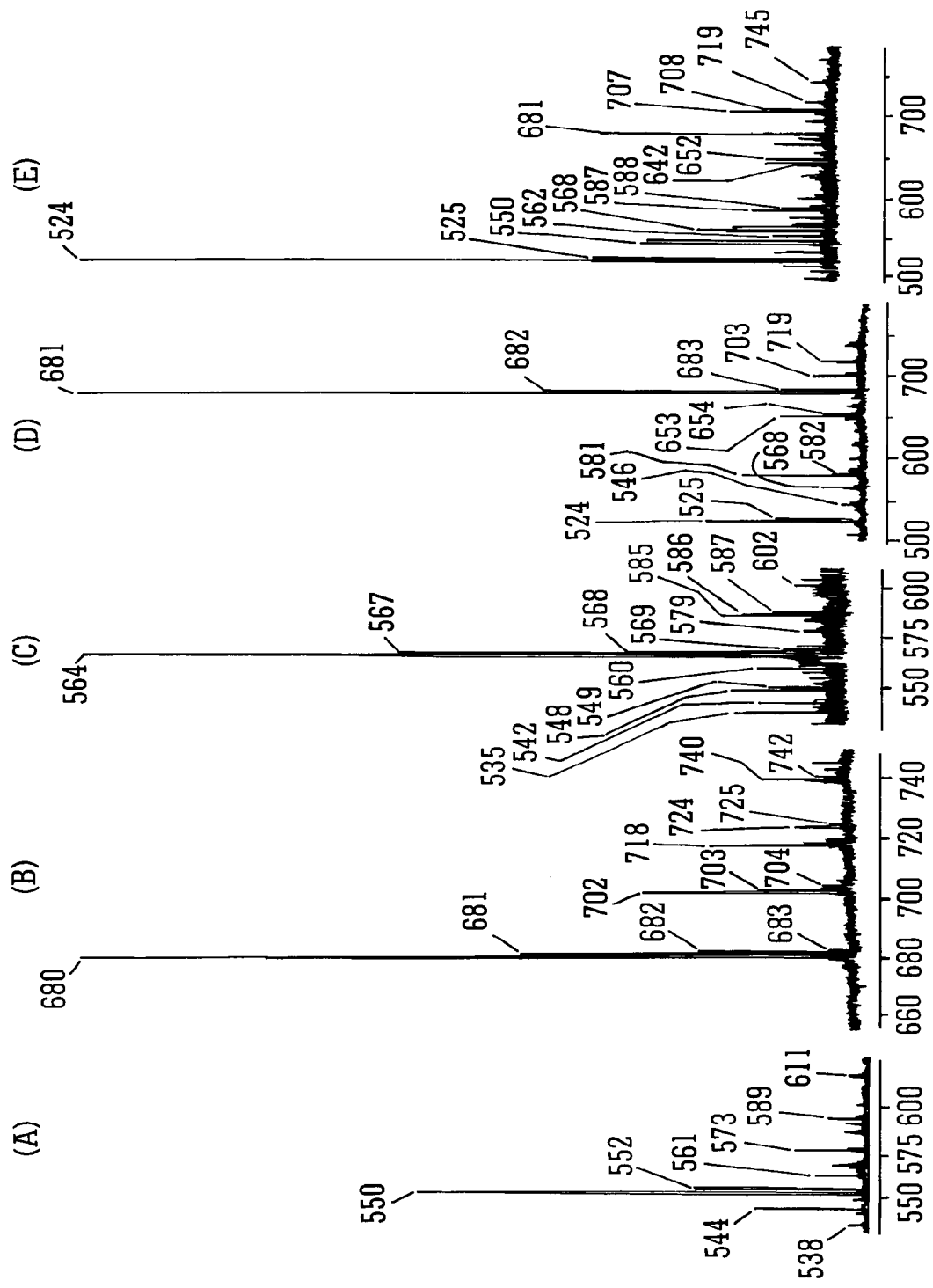
FIG. 9 (A) through 9(E) show multiple MALDI-TOF mass spectra for SEQ ID NO 2, the pentapeptide produced in Example 3.

In this example, a 1.2 mmol batch of TP-5 was produced which yielded more than 1 g of product (an overall yield of 94%). The purity of TP-5 produced by both MEPS and SPPS are illustrated in FIG. 8. The purity of MEPS product was estimated of ~94%, and MALDI-TOF analysis shown in FIG. 9 confirmed product's molecular weight of MH+ 650. The two impurities (at 10.0 minutes and 10.4 minutes) were identified as peptides resulting from the deletion of Asp, MH+ 564 and Lys, MH+ 550. The TP-5 produced by SPPS method under the same conditions of 2 equivalents reagents per 1 equivalent peptide and single reaction cycle, was only 77% pure. This result demonstrates the advantage of homogenous reaction in terms of lower excess of reagents required. The main impurity in SPPS was identified to be the deletion of Arg, MH+ 524.

EXAMPLE 4

A PEGylated oligonucleotide dimer was synthesised as an example of membrane enhanced oligonucleotide synthesis with a ceramic membrane. An Inopor zirconium oxide coated membrane with 3 nm pore size and hydrophobic surface modification (Inopor GmbH, Germany) was used in this example, using an apparatus as illustrated in FIG. 3.

Synthesis of 5'-O-Dmt-dTdA$^{Bz}$-3'succ-MeO-PEG

The rejection of relevant reactants was determined and shown in Table 2.

TABLE 2

Rejection data for PEGs and protected monomers used in oligonucleotide synthesis obtained with Inopor $ZrO_2/Al_2O_3$ ceramic membrane. The experiments were performed in a batch mode (or diafiltration mode when noted), and the rejection was determined according to Eq. 1.

| Compound | MW [g·mol⁻¹] | Inopor $ZrO_2/Al_2O_3$ Membrane Rejection [%] | Error[a] [%] | Flux [Lm⁻²h⁻¹] |
|---|---|---|---|---|
| 5'-O-Dmt-dA$^{Bz}$-3'-succinate | 757 | Monomer 55 | 7 | 170 |
| MeO-PEG | 5000 | Anchor 95 | 9 | 110 |
| 5'-O-Dmt-dA$^{Bz}$-3'succ-MeO-PEG[b] | 5739 | PEGylated monomer 96 | — | 45 |

[a]Error estimated from the mass balance between feed, permeate and retentate
[b]Diafiltration mode Synthesis of 5-O-(4,4-dimethoxytrityl)-2'-(N⁶-benzoyl) deoxyadenosine-3-succinate (5' O-Dmt-dA$^{Bz}$-3'succinate) (3). 5 g of 5'-O-Dmt-dA$^{Bz}$-3'-OH (1, 7.6 mmol) were co-evaporated with MeCN (2×10 mL) and dissolved in 85 mL of dry DCM. 4.2 mL of TEA (11.4 mmol) and 478 mg of DMAP, (3.9 mmol) were added to the solution, stirred under nitrogen atmosphere at room temperature. 11.4 g of succinic anhydride (2, 11.4 mmol) were then slowly added. The reaction was monitored using TLC (CHCl₃:MeOH, 9:1, v/v+0.5% TEA) and allowed to react until the starting nucleoside was completely consumed. The reaction was then quenched with an excess of water, stirred for 5 to 10 min. The reaction solution was then washed with 3×150 mL of water. The aqueous phase was then collected and extracted with 450 mL DCM (+0.5% v/v TEA). The organic phase was collected, dried over anhydrous MgSO₄, and evaporated to dryness to furnish white foam in high yields (90%), and product integrity was analysed by ¹H-NMR. The procedure is illustrated in Scheme 3.

Scheme 3 - Synthesis of 5'-O-Dmt-dA$^{Bz}$-3'-succinate:

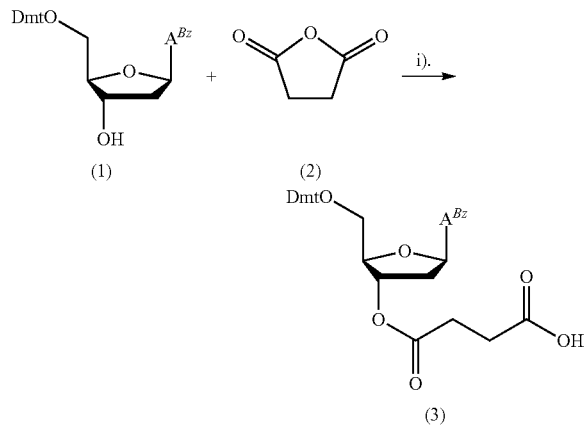

i). TEA, DMAP, DCM.

Figure 10:
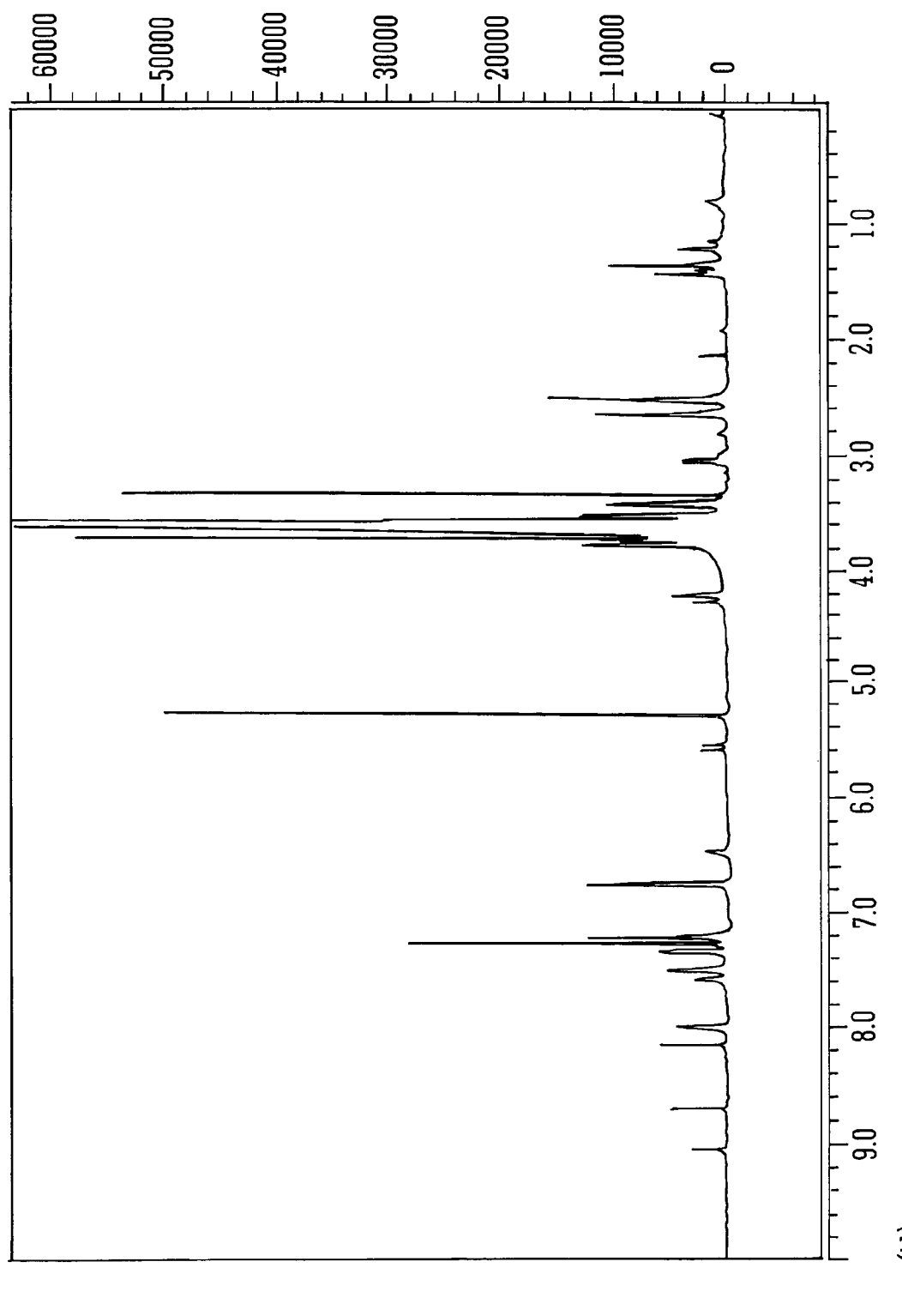
FIG. 10 shows NMR data from the dimeric oligonucleotide produced in Example 4.

Synthesis of 5-O-(4,4-dimethoxytrityl)-2-(N⁶-benzoyl) deoxyadenosine-3'succ-MeO-PEG (5-O-Dmt-dABz-3'succ-MeO-PEG) (5). (Scheme 4) 10 g of polyethylene glycol monomethyl ether (4, MeO-PEG, MW~5,000 g mol⁻¹ (2 mmol) and 4.5 g of 5'-O-Dmt-dA$^{Bz}$-3'-succinate (3, 6 mmol) were co-evaporated with dry MeCN (2×10 mL) and dissolved in 67 mL of dry DCM+0.5% (v/v) dry pyridine. 320 μL of NMI (4 mmol) and 530 μL of DIC (3.4 mmol) were added to the solution under stirring, and allowed to react under nitrogen atmosphere at room temperature for 24 h. The reaction solution was then filtered, evaporated to dryness and taken up in 100 mL of DCM+1% v/v TEA to be charged to the membrane separation apparatus. The reaction mixture was purified using 20 diafiltration volumes of solvent (DCM). The process was monitored with Gel Permeation Chromatography (GPC) and TLC (EtOAc:acetone:water, 5:10:1, v/v) and stopped when no low molecular weight species and high Rf species, respectively, where detected in the retentate. The product integrity and reaction conversion were analysed by ¹H-NMR (71%, FIG. 10).

Scheme 4 - Synthesis of 5'-O-Dmt-dA$^{Bz}$-3'succ-MeO-PEG:

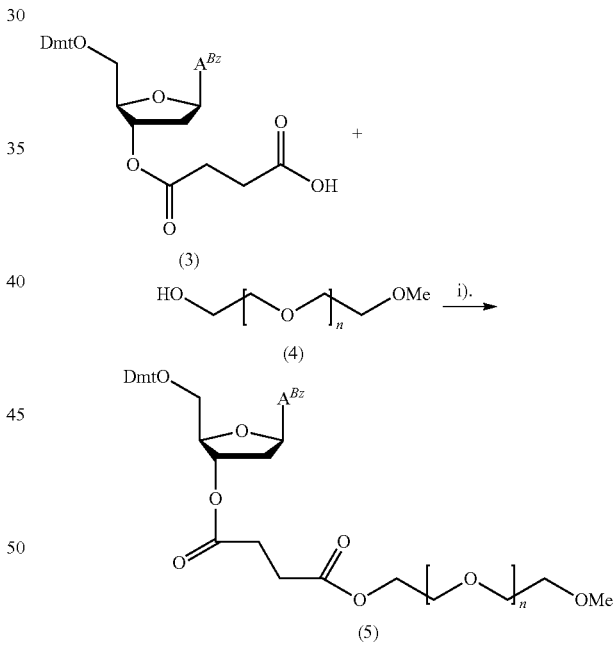

i). NMI, DIC, DCM + 0.5% pyridine.

Acetylation of 5-O-Dmt-dA$^{Bz}$-3'succ-MeO-PEG (Capping). 5 g of 5'-O-Dmt-dA$^{Bz}$-3'succ-MeO-PEG were dissolved in 25 mL of dry DCM in a round flask. The solution was stirred and ice-cooled, and 2,6-lutidine (2.5 mL), NMI (2.5 mL) and acetic anhydride (2.5 mL) were added. The reaction was allowed to react under nitrogen atmosphere for 30 min, after which it, was diluted to 100 mL DCM+1% v/v TEA and purified via membrane diafiltration using 5 volumes of solvent (DCM).

Detritylation of 5-O-Dmt-dA$^{Bz}$-3'succ-MeO-PEG. 3.7 g of 5'-O-Dmt-dA$^{Bz}$-3'succ-MeO-PEG (5) were co-evaporated with 2×10 mL of dry MeCN and dissolved in 19 mL of dry DCM. dissolved in 25 mL of dry DCM in a round flask. 900 μL of pyrrole (13 mmol) and 570 μL of DCA (3% v/v) were added to the stirring solution and allowed to react at room temperature under nitrogen atmosphere. The reaction was followed by TLC and, upon completion, quenched by the addition of an excess of TEA, diluted to make up 100 mL DCM+1% v/v TEA and purified using membrane diafiltration and 10 volumes of solvent (DCM), as in previous steps. Completion of detritylation was assessed by $^1$H-NMR.

Scheme 5 - Synthesis of 5'-OH-dA$^{Bz}$-3'succ-MeO-PEG:

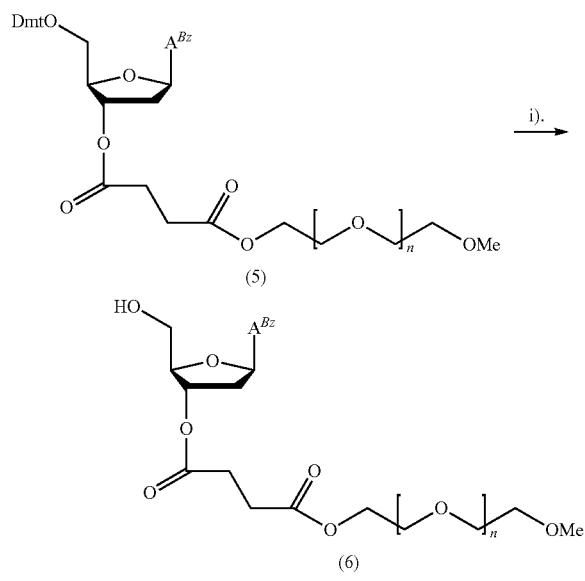

i). DCA, pyrrole, DCM.

Figure 11:
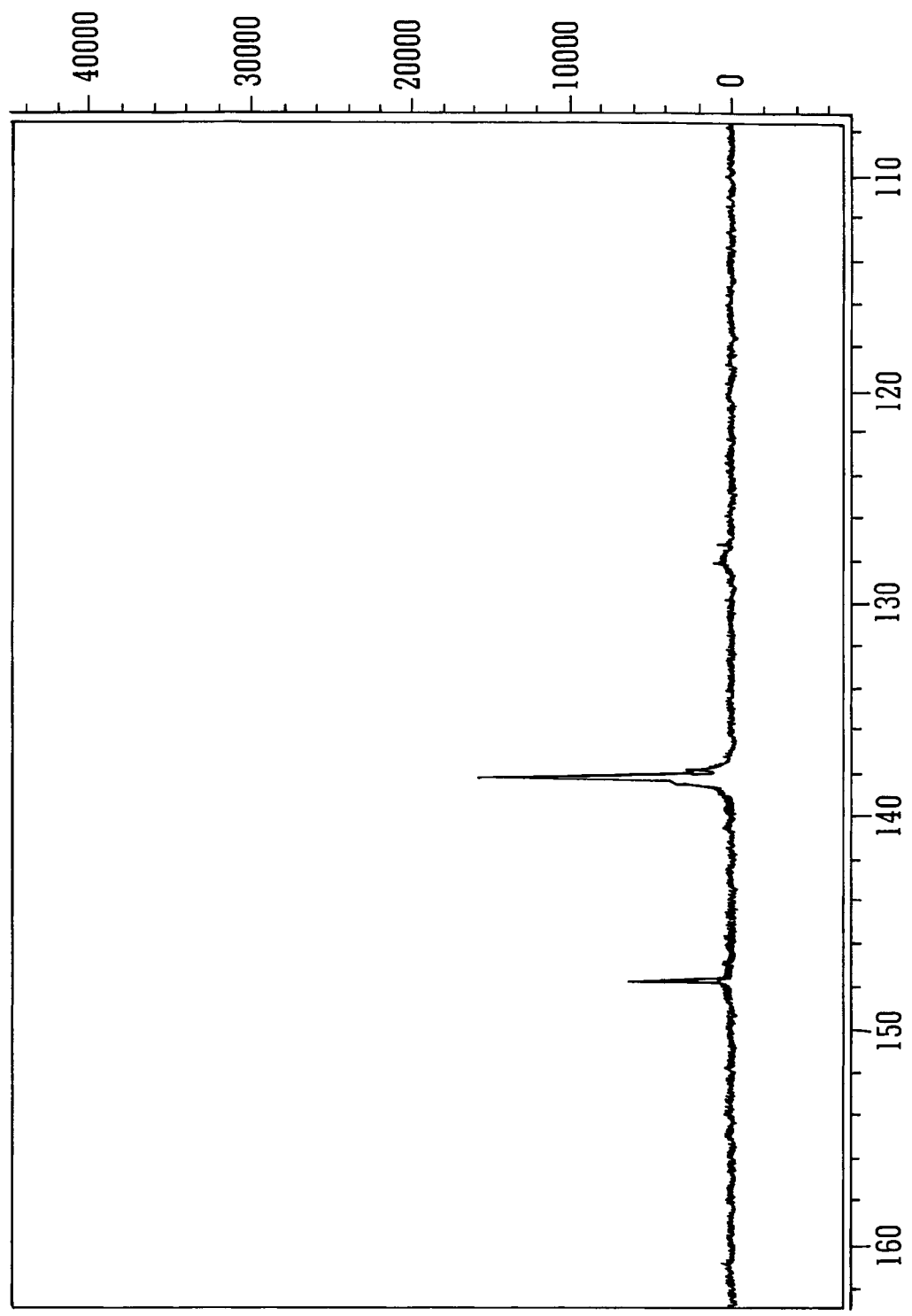
FIG. 11 shows NMR data from the dimeric oligonucleotide produced in Example 4.

Synthesis of 5-O-Dmt-dT-phosphite-dA$^{Bz}$-3'succ-MeO-PEG (7) (Scheme 5). 2.5 g of 5'-OH-dA$^{Bz}$-3'succ-MeO-PEG (5, 0.46 mmol) and 611 mg of 5'-O-(4,4'-dimethoxytrityl)-thymine-3'-(β-cyanoethyl-N,N'-diisopropylamino) phosphoramidite (6, 5'-O-Dmt-dT amidite, 0.8 mmol) were co-evaporated with 2×10 mL of dry MeCN and dissolved in 30 mL of dry MeCN. 65 μL of NMI (0.8 mmol) and 155 mg of PyTFA (0.8 mmol) were added to the stirring solution and allowed to react at room temperature under nitrogen atmosphere. The reaction was followed by TLC and, upon completion, quenched by the addition of an excess of TEA, evaporated and the crude analysed by $^1$H- and $^{31}$P-NMR (FIG. 11).

Scheme 5-Synthesis of 5'-O-Dmt-dT-phosphite-dA$^{Bz}$-3'succ-MeO-PEG:

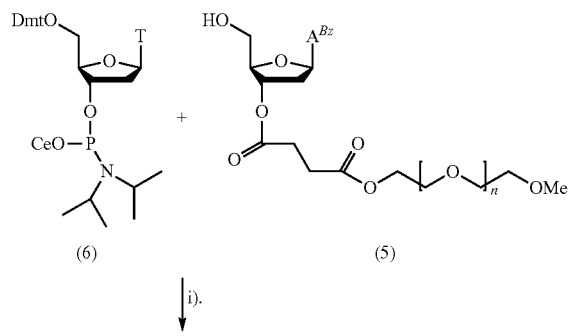

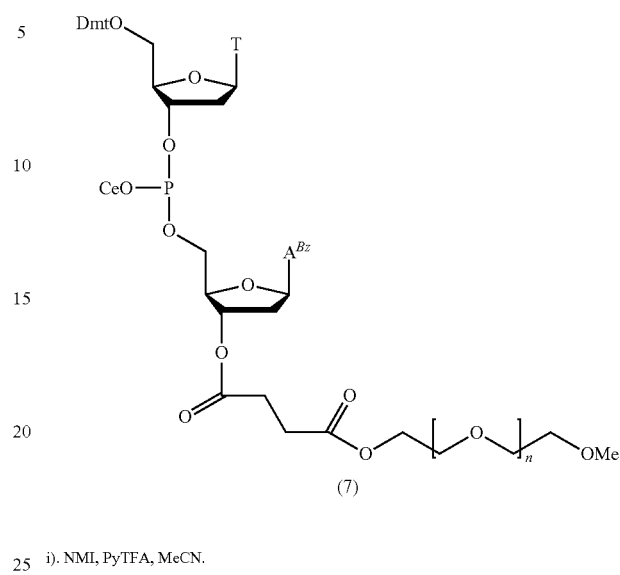

i). NMI, PyTFA, MeCN.

Oxidation of 5-O-Dmt-dT-phosphite-dg$^z$-3'succ-MeO-PEG. 5'-O-Dmt-dT-phosphite-dg$^z$-3'succ-MeO-PEG (7) was co-evaporated with MeCN (2×5 mL) and dissolved in a 1.1M TBHP solution in DCM, and allowed to react at room temperature and nitrogen atmosphere for 15 min. The solution was evaporated, taken up in 100 mL of DCM, and membrane purified using 20 volumes of solvent (DCM), as in previous steps, to furnish 1.2 g of PEGylated dimer (8).

Scheme 6-Synthesis of 5'-O-Dmt-dTdA$^{Bz}$-3'succ-MeO-PEG:

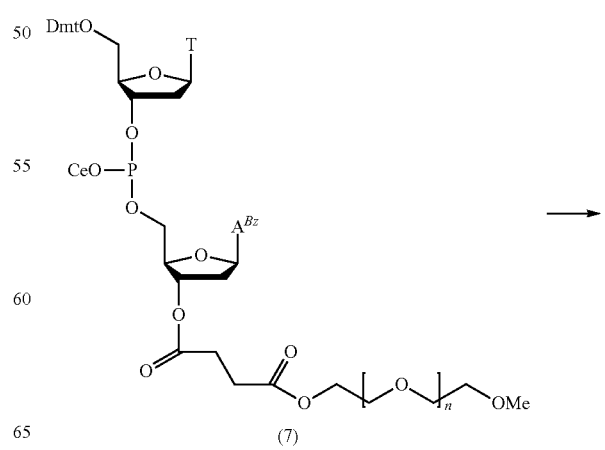

-continued

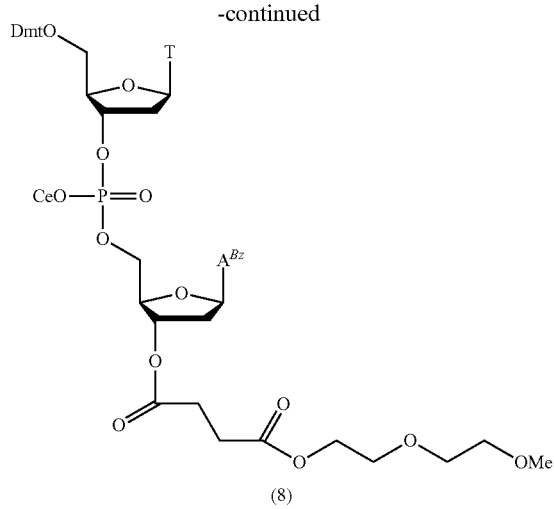

(8)

i). TBHP, DCM.

The invention claimed is:

1. A process for the preparation of a first compound selected from peptides, oligonucleotides, and peptide nucleic acids; the process comprising: (i) synthesising the first compound by liquid phase synthesis in an organic solvent; and (ii) separating the first compound formed in step (i) from a second compound, which is a reaction by-product of the synthesis of the first compound and/or an excess of a reagent used for the synthesis of the first compound, wherein (a) the synthesis of the first compound in step (i) involves one or more coupling or deprotection reactions; (b) the first and second compounds are dissolved in an organic solvent and are separated by a process of diafiltration using a membrane that is stable in the organic solvent and which provides a rejection for the first compound which is greater than the rejection for the second compound; and (c) the process comprises subjecting the first compound to one or more coupling and/or deprotection reactions subsequent to separation.

2. A process according to claim 1, wherein the organic solvent for the liquid phase synthesis is the same as that used for the diafiltration.

3. A process according to claim 1, which further comprises purifying the product of (c) using a diafiltration process as defined in step (ii).

4. A process according to claim 1, wherein the membrane is a polymeric membrane.

5. A process according to claim 1, wherein the membrane is a ceramic membrane.

6. A process according to claim 1, wherein the membrane is a mixed matrix organic/inorganic membrane.

7. A process according to claim 1, wherein the first compound is attached to a support.

8. A process according to claim 7, wherein the support is a polymer support.

9. A process according to claim 8, wherein the support comprises a dendrimer or hyperbranched polymer.

10. A process according to claim 7, wherein the support is an organic or inorganic nanoparticle.

11. A process according to claim 1, wherein the first compound has a molecular weight greater than 500 daltons.

12. A method of use of a filtration membrane for the preparation of a first compound selected from peptides, oligonucleotides, and peptide nucleic acids; the method comprising:
(i) synthesising the first compound;
(ii) separating the first compound formed in step (i) from an organic solvent and a second compound, which is a reaction by-product of the synthesis of the first compound and/or an excess of a reagent used for the synthesis of the first compound, wherein the first and second compounds are dissolved in an organic solvent and are separated by a process of diafiltration using a membrane that is stable in the organic solvent and which provides a rejection for the first compound which is greater than the rejection for the second compound; and
(iii) subjecting the first compound to one or more coupling and/or deprotection reactions subsequent to separation.

* * * * *

SEQUENCE LISTING

<160> NUMBER OF SEQ ID NOS: 2

<210> SEQ ID NO 1
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 1

Tyr Ala Tyr Ala Tyr
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 2

Arg Lys Asp Val Tyr
1               5